United States Patent [19]

Sinay, Jr. et al.

[11] Patent Number: 4,904,782
[45] Date of Patent: Feb. 27, 1990

[54] PROCESS FOR THE PRODUCTION OF PHTHALAZINEACETIC ACID ESTER DERIVATIVES AND A NOVEL INTERMEDIATE

[75] Inventors: Terry G. Sinay, Jr., Preston; Robert J. Sysko, Niantic, both of Conn.

[73] Assignee: Pfizer Inc., New York, N.Y.

[21] Appl. No.: 161,540

[22] Filed: Feb. 29, 1988

[51] Int. Cl.$^4$ .................. C07B 43/00; C07B 43/06; C07D 237/32; C07D 237/34
[52] U.S. Cl. .................................................. 544/237
[58] Field of Search ........................................ 544/237

[56] References Cited

U.S. PATENT DOCUMENTS 4,251,528  2/1981  Brittain et al. .................. 424/250

FOREIGN PATENT DOCUMENTS 222576  5/1987  European Pat. Off. .

OTHER PUBLICATIONS

Schroeder et al., Condensation of Phthalideneacetic Acid with Napthalenes to form Benzopyrenequinones, J. Amer. Chem. Soc., 78, 446 (1956).
Vaughn et al., The Preparation of Some Phthalazines and Related Substances, J. Amer. Chem. Soc., 68, 1314 (1946).
Foldeak et al., Phthalazines and Related Heterocycles. IX. Derivatives of 4(3H)-Phthalazone-4-acetic Acid, Chem. Abs. 72:100626p (1970).

Primary Examiner—Mark L. Berch
Attorney, Agent, or Firm—Peter C. Richardson; J. Trevor Lumb; Gregg C. Benson

[57] ABSTRACT

This invention relates to a process for the production of phthalazineacetic acid ester derivatives of the formula

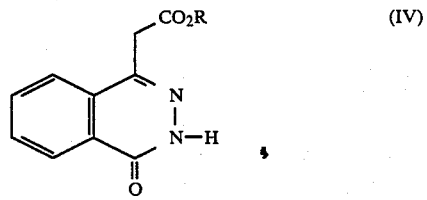

(IV)

wherein R is ($C_1$–$C_4$) alkyl which comprises reacting (Z)-3-oxo-1(3H)-isobenzofuranylideneacetic acid with hydrazine in the presence of a solvent; reacting the resulting mixture of the novel compound 1-hydrazino-1,2,3,4-tetrahydro-4-oxo-phthalazineacetic acid and 3,4-dihydro-4-oxo-phthalazineacetic acid with acid in the presence of a solvent; and reacting the resulting 3,4-dihydro-4-oxo-phthalazineacetic acid with acid in the presence of an alcohol.

This invention also relates to the novel compound 1-hydrazino-1,2,3,4-tetrahydro-4-oxo-phthalazineacetic acid of the formula

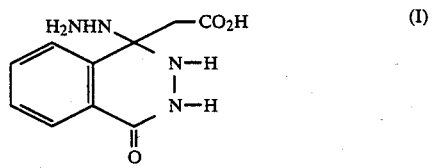

(I)

which is an intermediate formed in the process of this invention and which is useful for the production of phthalazineacetic acid ester derivatives of formula IV. The compounds of formula IV are useful for the preparation of certain heterocyclic oxophthalazinyl acetic acids and esters thereof.

22 Claims, No Drawings

PROCESS FOR THE PRODUCTION OF PHTHALAZINEACETIC ACID ESTER DERIVATIVES AND A NOVEL INTERMEDIATE

BACKGROUND OF THE INVENTION

1. Field of the Invention

This invention relates to a process for the production of phthalazineacetic acid ester derivatives of the formula

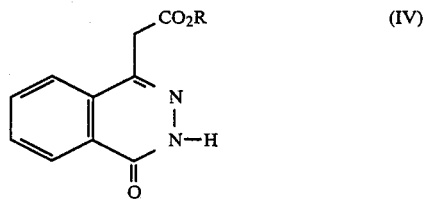

wherein R is $(C_1-C_4)$alkyl.

This invention also relates to the novel compound 1-hydrazino-1,2,3,4-tetrahydro-4-oxo-phthalazineacetic acid of the formula

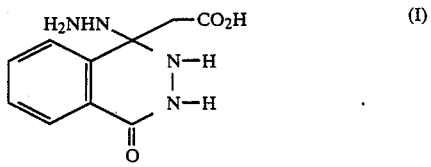

which is an intermediate formed in the process of this invention and which is useful for the production of phthalazineacetic acid ester derivatives of formula IV. The compounds of formula IV are useful for the preparation of certain heterocyclic oxophthalazinyl acetic acids and esters thereof.

2. General Background

Certain heterocyclic oxophthalazinyl acetic acids and esters of the general formula

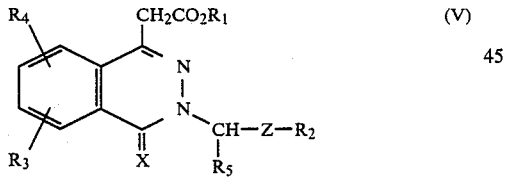

wherein X is oxygen or sulfur, Z is a covalent bond, O, S, NH or $CH_2$; $R_1$ is hydroxy, or a prodrug group; $R_2$ is a heterocyclic group, $R_3$ and $R_4$ are hydrogen or the same or a different substituent, and $R_5$ is hydrogen or methyl, as well as certain pharmaceutically acceptable salts thereof and their usefulness as inhibitors of aldose reductase are disclosed in pending U.S. patent application Ser. No. 916,127, filed Oct. 7, 1986 which is a divisional application of Ser. No. 796,039, filed Nov. 7, 1985, now abandoned, and which is assigned to the assignee hereof and, inter alia, in the corresponding published European Patent Application No. 222,576, published May 20, 1987, wherein the applicant is the assignee hereof. The teachings thereof are incorporated herein by reference. That patent application also discloses a process for the production of certain phthalazineacetic acid esters which comprises reacting certain phthalic anhydrides with either (carbethoxymethylene)triphenylphosphorane or (carbomethoxymethylene)triphenylphosphorane in the Wittig reaction and then reacting the resulting acetic acid ester derivatives with hydrazine in, preferably, an aqueous solvent at 40° to 120° C.

A process for preparation of (Z)-3-oxo-1(3H)-isobenzofuranylideneacetic acid from phthalic anhydride by reacting phthalic anhydride with potassium acetate and acetic anhydride is disclosed by Schroeder, H. E., et al., J. Amer. Chem. Soc., 78, 446 (1956). and acetic anhydride is disclosed by Schroeder, H. E., et al., J. Amer. Chem. Soc., 78, 446 (1956).

A process for the preparation of certain phthalazones by reacting orthophthalaldehydic acid or phthalonic acid with hydrazine is disclosed by Vaughan, W. R. and Baird, Jr., S. L., J. Amer. Chem. Soc., 68, 1314 (1946).

Foldeak, S., et al., Chemical Abstracts 72: 100626 p (1970), Khim.-Farm. Zh, 3(12), 5 (1969), disclose, inter alia, a process for the preparation of 4(3H)-phthalazone-1-acetic acid by heating (Z)-3-oxo-1(3H)-isobenzofuranylideneacetic acid for two (2) hours with $N_2H_4$—$H_2SO_4$ in aqueous $KHCO_3$.

SUMMARY OF THE INVENTION

This invention concerns a process for the production of phthalazineacetic acid ester derivatives of the formula

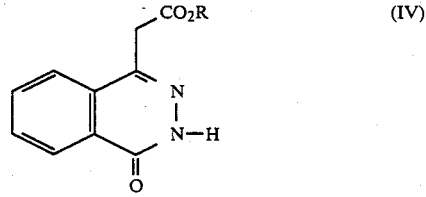

where R is $(C_1-C_4)$alkyl which comprises reacting (Z)-3-oxo-1(3H)-isobenzofuranylideneacetic acid of the formula

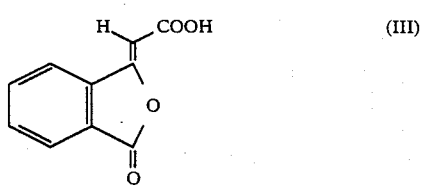

with hydrazine in the presence of a solvent to form a mixture comprising the novel intermediate 1-hydrazino-1,2,3,4-tetrahydro-4-oxo-phthalazineacetic acid of the formula

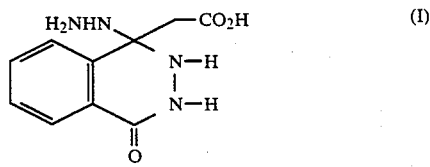

and 3,4-dihydro-4-oxo-phthalazineacetic acid of the formula

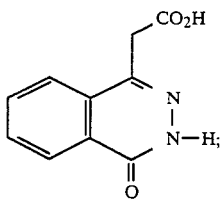

(II)

reacting the mixture so obtained with acid in the presence of a solvent to convert the 1-hydrazino-1,2,3,4-tetrahydro-4-oxo-phthalazineacetic acid to 3,4-dihydro-4-oxo-phthalazineacetic acid; and reacting the 3,4-dihydro-4-oxo-phthalazineacetic acid with acid in the presence of an alcohol of the formula ROH, where R is as defined above, to yield compounds of the formula IV.

This invention also concerns a process for the production of the novel intermediate of formula I which comprises reacting (Z)-3-oxo-1(3H)-isobenzofuranylideneacetic acid of formula III with hydrazine in the presence of a solvent.

Further, this invention concerns processes for the production of 3,4-dihydro-4-oxo-phthalazineacetic acid of formula II which comprise (a) reacting (Z)-3-oxo-1(3H)-isobenzofuranylideneacetic acid of formula III with hydrazine in the presence of a solvent or (b) reacting the mixture of compounds of formulae I and II with acid.

The phthalazineacetic acid esters so produced by the process of this invention are useful as intermediates in the preparation of certain heterocyclic oxophthalazinyl acetic acids and esters such as certain of those of formula V, above.

DETAILED DESCRIPTION OF THE INVENTION

The overall process of this invention is comprised of several processes shown as reaction steps (1-4) in Reaction Scheme A below. The starting compound (III) is prepared from phthalic anhydride, acetic anhydride and potassium acetate pursuant to the reaction described by Schroeder, et al., J. Amer. Chem. Soc., 78, 446(1956). In reaction step 1, (Z)-3-oxo-1(3H)-isobenzofuranylideneacetic acid of formula III is reacted in the form of a slurry with hydrazine in the presence of a solvent. Suitable solvents are those in which the reactants are at least partially soluble. Preferably, the solvent used is a lower alkyl alcohol with the most preferred solvent being ethanol. However, it is to be understood that other appropriate reaction inert solvents well known to those skilled in the art can be used. It is also preferred that two (2) mole equivalents of hydrazine be used in the reaction. The temperature of this reaction rises due to exotherm. Therefore, in order to reduce formation of unwanted pyrazolone hydrazide and owing to the explosive nature of hydrazine, it is preferred to control the temperature of the reaction to less than about 40° C. Still more preferably, the reaction temperature is controlled to from about 20° C. to about 30° C. with an even more preferred temperature range of about 25° C. to about 30° C. The reaction of step 1 results in the production of a mixture of 3,4-dihydro-4-oxo-phthalazineacetic acid of formula II and the novel compound 1-hydrazino-1,2,3,4-tetrahydro-4-oxo-phthalazineacetic acid of formula I which mixture can be recovered by filtration, washed and dried, all by conventional means well known to those skilled in the art, to yield the mixture was solids.

While, under certain isolation conditions hydrazine is lost from compound of formula I to generate the compound of formula II, the novel compound 1-hydrazino-1,2,3,4-tetrahydro-4-oxo-phthalazineacetic acid (I) is nevertheless useful in producing the desired ester of formula IV, above since isolation of that compound away from 3,4-dihydro-4-oxo-phthalazineacetic acid (II) of the mixture is not necessary or preferred for use of the compound of formula I and/or for the novel process of this invention. According to the conditions described herein, when (Z)-3-oxo-1(3H)-isobenzofuranylideneacetic acid III is reacted with hydrazine, mixtures containing >80% I and <20% II are recovered based on high yield NMR assay.

REACTION SCHEME A

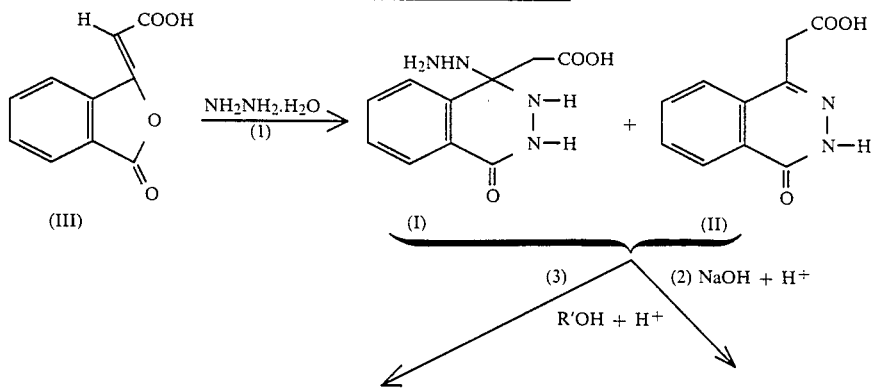

-continued
REACTION SCHEME A

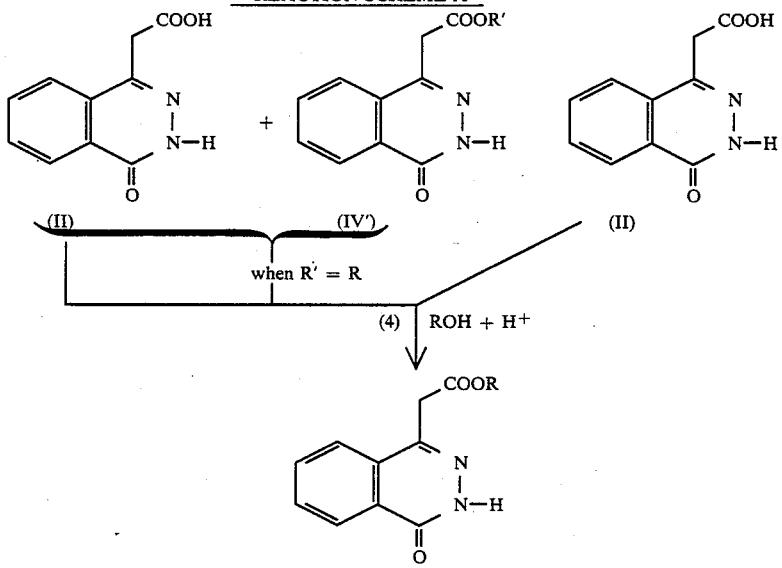

After the compounds of formulae I and II have been produced according to reaction step 1, the scheme for the process of this invention branches into two alternate routes shown in Reaction Scheme A as steps 2 and 4 or steps 3 and 4.

According to the route encompassing steps 2 and 4, the mixture of 3,4-dihydro-4-oxo-phthalazineacetic acid (II) and 1-hydrazino-1,2,3,4-tetrahydro-4-oxo-phthalazineacetic acid (I) is dissolved in water or aqueous NaOH, heated to about 40° C., cooled to room temperature and acidified, preferably with hydrochloric acid, to convert the hydrazino adduct to 3,4-dihydro-4-oxo-phthalazineacetic acid (II). Following granulation, which commences upon addition of the acid, the product as a solid is recovered by standard techniques such as filtration and is then washed and dried. The resulting 3,4-dihydro-4-oxo-phthalazineacetic acid (II) is then reacted with acid in the presence of solvent ROH where R is $(C_1-C_4)$alkyl to produce the ester of formula IV. Preferably, the acid used is anhydrous hydrochloric acid. Still more preferably, the reaction is heated to reflux temperature of the alcohol solvent and about 1.0 mole equivalent of anhydrous hydrochloric acid is used. Yet more preferably still, the solvent is methanol or ethanol. As used throughout this specification and appendant claims, the term ethanol shall include absolute ethanol as well as the other commercially available ethanols such as 2B ethanol.

Alternatively and preferably, the mixture of 1-hydrazino-1,2,3,4-tetrahydro-4-oxo-phthalazineacetic acid (I) and 3,4-dihydro-4-oxo-phthalazineacetic acid (II) is reacted with acid in the presence of a solvent R'OH where R' is $(C_1-C_4)$alkyl. This reaction, which is shown as step 3 in Reaction Scheme A, results in the production of a mixture of 3,4-dihydro-4-oxo-phthalazineacetic acid (II) and the ester of formula IV'.

Since some ester of formula IV' is formed as a result of this reaction, it is preferable to choose an appropriate solvent such that the desired ester of formula IV is so formed. Therefore, it is preferred to use a solvent R'OH for this reaction where R' corresponds to the value for R in the ultimate ester product of formula IV. In this way, additional steps for purification of 3,4-dihydro-4-oxo-phthalazineacetic acid (II) away from the ester of formula IV' will not be necessary. It is also preferable to use anhydrous hydrochloric acid in the process of step 3. Even more preferred is to use about 1.0 mole equivalent of anhydrous hydrochloric acid and to heat the reaction to reflux temperature of the solvent. More preferred still is to employ methanol or ethanol as the solvent. If R' equals R, then the mixture of compounds II and IV' produced as a result of reaction step 3 need not be isolated but, instead, are reacted with additional acid in the same solvent. Here, too, it is preferable to used anhydrous hydrochloric acid. And, still more preferably, about 1.0 mole equivalent of additional anhydrous hydrochloric acid is added and the reaction heated to reflux temperature of the solvent. The ester is then recovered by standard techniques such as filtration, then washed and dried. If necessary or desired, the resulting solid can be further purified by standard techniques. For example, the solid product can be repulped in water, recovered by filtration with chloroform extractions of the aqueous filtrate and the extractions combined with the filter cake in chloroform. The chloroform solution can then be subjected to Darco treatment, distilled at about 60° to 64° C. with step additions of hexane to yield a slurry. The slurry is then cooled to about 25° C. and allowed to granulate. The solids are recovered by standard techniques such as filtration, then washed and dried to yield the ester as a solid.

If R' is not equal to R, the compounds II and IV' must be separated which separation can be achieved according to methods well known to those skilled in the art. Then, the isolated 3,4-dihydro-4-oxo-phthalazineacetic acid (II) is reacted with acid in the presence of a solvent ROH as described above to give the corresponding ester IV.

The following examples serve to illustrate the invention and are not to be construed as limiting the scope of this invention to the embodiments so exemplified. Nuclear magnetic resonance spectra (NMR) were measured for solutions in deuterated dimethyl sulfoxide (DMSO-$d_6$) and peak positions are expressed in parts per million (ppm) downfield from tetramethylsilane.

The peak shapes are denoted as follows: s, singlet; t, triplet; q, quartet; m, multiplet.

PREPARATION A

(Z)-3-Oxo-1(3H)-isobenzofuranylideneacetic Acid

To 402 ml (4.26 moles) of acetic anhydride was added 150.0 g (1.01 moles) of phthalic anhydride and 124 g (1.26 moles) of potassium acetate in a 2 liter 3 neck flask. The resulting slurry was heated to 130°–135° C. for 1 hour and 20 minutes then cooled to 75°–80° C. and 1500 ml of toluene were added. The slurry was allowed to cool to 30° C. and granulate for 1 hour. The solids were recovered by filtration, washed with 300 ml of methylene chloride and air dried. The dried solids were repulped in 1500 ml $H_2O$ at 20°–25° C., allowed to granulate for 1 hour and oven dried at 50° C. overnight with an air bleed to give a yield of 52% (100.0 g) of the title compound:

mp 245°–250° C.;

NMR (DMSO-$d_6$, 60 mHz): δ7.68–8.5 (m, 4, AR—$\underline{H}$); 6.33 (s, 1,

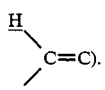

).

EXAMPLE 1

3,4-Dihydro-4-oxo-phthalazineacetic Acid and 4-Hydrazino-1,2,3,4-tetrahydro-4-oxo-phthalazineacetic Acid A.(i) To 250 ml of ethanol (2B) in a 500 ml round bottom flask was added 25 g (132 mmoles) of (Z)-3-oxo-1(3H)-isobenzofuranylideneacetic acid. To the resulting slurry was added 11.8 ml of a 54% solution of hydrazine (132 mmoles) in ethanol (2B) at 25° C. over 10 minutes. The reaction was stirred for 30 minutes and a sample removed for thin layer chromatography (TLC) using a 4:1:2 chloroform/methanol/acetic acid system which showed two products were produced. The reaction slurry was filtered, washed with 50 ml of ethanol (2B) and dried in a vacuum oven at 40° C. with a nitrogen bleed to give 25.2 g grams of solid mixture. Thin layer chromatography using 4:1:0.1 chloroform/methanol/acetic acid revealed that this solid mixture consisted of two quite polar compounds. The more polar compound was identified as 3,4-dihydro-4-oxo-phthalazineacetic acid by comparison with an authentic sample prepared by saponification of the ethyl ester derivative. The less polar compound of the mixture was characterized by the following experiments:

A.(ii) To 50 ml of methylene chloride in a 125 ml 3 neck round bottom flask equipped with a mechanical stirrer, thermometer and reflux condenser was added 10 g of the solid mixture obtained in A.(i), above. The flask was heated to reflux (about 40° C.) and refluxed for 1 hour, cooled to room temperature and the contents rapidly filtered onto a Buchner funnel. The solids were washed twice with 25 ml of methylene chloride per wash and dried in a vacuum oven at about 40° C. with a nitrogen bleed for 2 hours to give 9 g (90% recovery) of the solid mixture virtually unchanged.

A.(iii) To 42.5 ml of methylene chloride in a 150 ml 3 neck round bottom flask equipped with a mechanical stirrer, thermometer and reflux condenser was added 8.5 g of the solid mixture obtained in A.(ii), above. The flask was heated to reflux (about 40° C.) and refluxed for 1 hour and then allowed to slowly cool to room temperature. The contents were allowed to granulate for 1 hour, then filtered onto a Buchner funnel, washed twice with 21.25 ml of methylene chloride per wash and dried in a vacuum oven at about 40° C. with a nitrogen bleed to give 8.06 g (94.8% recovery) of tan solid. TLC using 4:1:0.1 chloroform/methanol/acetic acid once again revealed that this solid was a mixture of two compounds with the same less polar compound described above as the major constituent. When a 300 mHz NMR was obtained for the mixture in DMSO-$d_6$, in addition to the singlet corresponding to the methylene protons of 3,4-dihydro-4-oxo-phthalazineacetic acid at δ3.64, two non-equivalent methylene protons were observed at δ2.74 and δ2.27, indicating that they were bound to an asymmetric carbon as well as to an acid function. According to combustion analysis the solid mixture contained 23.7% nitrogen, demonstrating that a second hydrazine molecule had been incorporated. The structure of the second novel compound, 1-hydrazino-1,2,3,4-tetrahydro-4-oxo-phthalazineacetic acid (I), was determined from this analytical data.

EXAMPLE 2

3,4-Dihydro-4-oxo-phthalazineacetic Acid and 1-Hydrazino-1,2,3,4-tetrahydro-4-oxo-phthalazineacetic Acid To 500 ml of ethanol (2B) in a 1 liter 3 neck flask was added 50.0 g (263 mmole) of (Z)-3-oxo-1(3H)-isobenzofuranylideneacetic acid. Then, 31 ml (526 mmol, 2 eq) of 54.4% hydrazine in ethanol (2B) was added to the flask over 10–15 minutes whereupon the temperature of the reaction rose to 41° C. due to an exotherm. The slurry was stirred for 1.5 hours at 25°–30° C., filtered, washed with 100 ml of ethanol (2B) and oven dried overnight at 40° C. with vacuum and a nitrogen bleed to give 57.79 g of a mixture of the title compounds.

EXAMPLE 3

3,4-Dihydro-4-oxo-phthalazineacetic Acid and 1-Hydrazino-1,2,3,4-tetrahydro-4-oxo-phthalazineacetic Acid To 500 ml of ethanol (2B) in a 1 liter 3 neck flask was added 50.0 g (263 mmoles) of (Z)-3-oxo-1(3H)-isobenzofuranylideneacetic acid. Then, 23 ml of a 54% solution of hydrazine (395 mmoles) in ethanol (2B) was added slowly over 10 minutes. The reaction temperature rose to 42° C. due to an exotherm and was allowed to cool to room temperature and stirred for 1.5 hours. The resulting solids were recovered by filtration, washed with 100 ml of ethanol (2B) and dried overnight in a vacuum oven at 40° C. with a nitrogen bleed to give 47.14 g of a mixture of the title compounds as solids.

EXAMPLE 4

3,4-Dihydro-4-oxo-phthalazineacetic Acid

The pH of an aqueous solution comprising 4.50 g of the mixture of 3,4-dihydro-4-oxo-phthalazineacetic acid and 4-hydrazino-3,4-dihydrophthalazine acetic acid prepared as described in Example 1, Part A.(i) was adjusted from pH 6.0 to 1.5 with 12N aqueous HCl. Crystallization occured within a few minutes and the resulting slurry was granulated 1 hour at room temperature. The solid was collected by filtration, washed with water, and dried to afford 1.01 g of pure compound II:

mp 179°-181° C.;
Anal. Calc'd. for $C_{10}H_8N_2O_3$: C, 58.82; H, 3.95; N, 13.72. Found: C, 59.23; H, 3.92; N, 13.56.

EXAMPLE 5

3,4-Dihydro-4-oxo-phthalazineacetic Acid

To 12 ml of $H_2O$ and 6 ml of 12.5% NaOH in an Erlenmeyer flask with a magnetic stirrer and heater was added 0.3 g of a mixture of 3,4-dihydro-4-oxo-phthalazineacetic acid and 1-hydrazino-1,2,3,4-tetrahydro-4-oxo-phthalazineacetic acid obtained in Example 1, Part A.(i). The solution was filtered, heated to 40° C., cooled to room temperature and then acidified with 20 ml of 3N HCl whereupon solids began to form. After 0.5 hours of granulation, the solids were filtered onto a Buchner funnel, washed twice with $H_2O$ and dried in a vacuum oven at 40° C. with a nitrogen bleed. The mother liquor from the above reaction was stored overnight, whereupon thin white crystals formed. The crystals were recovered by filtration and washed with $H_2O$. Thin layer chromatography revealed that the first crop product was primarily 3,4-dihydro-4-oxo-phthalazineacetic acid with a trace of the corresponding hydrazine adduct of formula (I), while the crystals isolated as the second crop were only 3,4-dihydro-4-oxo-phthalazine acetic acid.

EXAMPLE 6

3,4-Dihydro-4-oxo-phthalazineacetic Acid

Into a 500 ml 3 neck round bottom flask with a nitrogen atmosphere and outfitted with a mechanical stirrer, thermometer, thermowatch and heating mantle were placed 250 ml of ethanol (2B) and 25 g (0.106 mole) of a mixture of 3,4-dihydro-4-oxo-phthalazineacetic acid and 1-hydrazino-1,2,3,4-tetrahydro-4-oxo-phthalazineacetic acid. Then, 1.929 g (0.053 mole, 0.5 eq) of HCl was bubbled into 50 ml of ethanol (2B) and that solution was added to the flask. The flask was heated to 60° C. and the reaction was allowed to proceed for about 22 hours at which time a sample was removed and analyzed by thin layer chromatography (TLC) (12:3:1 chloroform/methanol/acetic acid), 254 nm. The TLC revealed that there was no remaining 1-hydrazino-1,2,3,4-tetrahydro-4-oxo-phthalazineacetic acid present but, primarily, 3,4-dihydro-4-oxo-phthalazineacetic acid with some ethyl ester thereof also present.

EXAMPLE 7

3,4-Dihydro-4-oxo-phthalazineacetic , Ethyl Ester

Into a 500 ml 3 neck round bottom flask with a nitrogen atmosphere and outfitted with a mechanical stirrer, thermometer, thermowatch and heating mantle was placed 250 ml of ethanol (2B) and 25 g (0.106 mole) of a mixture of 3,4-dihydro-4-oxo-phthalazineacetic acid and 1-hydrazino-1,2,3,4-tetrahydro-4-oxo-phthalazineacetic acid. Then, 0.386 g (0.0106 mole, 0.1 eq) of HCl was bubbled into 50 ml of ethanol (2B) and that solution was added to the flask. The reaction mixture was heated to reflux (78° C.) for about 3 hours, then cooled to 39° C. TLC (12:3:1 chloroform/methanol/acetic acid) of a sample from the reaction mixture after three hours revealed that there was no TLC detectable 1-hydrazino-1,2,3,4-tetrahydro-4-oxo-phthalazineacetic acid remaining but, primarily, 3,4-dihydro-4-oxo-phthalazineacetic acid with some ethyl ester thereof also present. Then, 3.85 g (0.106 mole, 1 eq) of HCl gas was bubbled into the reaction mixture and the reaction was again heated to reflux for about 4.75 hours whereupon the reaction mixture was allowed to cool and stir overnight at 23° C. The solids were filtered off and washed once with 50 ml of ethanol (2B) and dried in a vacuum drier at 40° C. to give 26.1 g of light tan solids. A sample was then analyzed by HPLC (Nova Pak* $C_{18}$ column; 55% 0.05M $KH_2PO_4$(pH 3), 25% $CH_3CN$, 20% $CH_3OH$; flow rate: 0.35 ml/min.; monitor UV-229 nm) which showed the solids to be, by area percent, 1.74% 3,4-dihydro-4-oxo-phthalazineacetic acid, 2.09% 4-methyl-1(2H)-phthalazinone and 95.99% 3,4-dihydro-4-oxo-phthalazineacetic acid, ethyl ester with peak retention times of 2.86 min., 4.13 min. and 5.66 min., respectively. All 26.1 g of the light tan solids obtained above were added to 210 ml of $H_2O$ at 23° C. and repulped for about 30 minutes. Then, the solids were recovered by fast filtration through cotton cloth with one 40 ml $H_2O$ wash. The $H_2O$ filtrate was extracted with chloroform (2×65 ml), the chloroform extractions were combined with the wet cake of solids and additional chloroform was added to bring the total volume up to 500 ml. The solution was stirred and then allowed to separate into two layers. The aqueous layer was extracted once with 50 ml of chloroform and the chloroform phase was combined with the chloroform solution above. To the chloroform solution was added 1.2 g Darco G-60, 2.5 g $MgSO_4$ and 2.5 g filter cell. Then the mixture was filtered through cotton cloth and washed once with 100 ml of chloroform. The filtrate and wash were combined and distilled atmospherically at about 60°-64° C. for about 30 minutes with dropwise additions of 100 ml, 150 ml and 150 ml of hexane after about 20 minutes, 25 minutes and 27 minutes, respectively. The resulting slurry was cooled to 25° C. and granulated for 2 hours. The solids were removed by filtration, washed with 125 ml hexane and dried in a vacuum oven at 40° C. to give the title compound as an off-white solid:

m.p. 177°-179° C.

NMR (DMSO-$d_6$, 300 mHz): δ12.68 (s, 1, N—$\underline{H}$); 8.24-7.89 (m, 4, AR—H); 4.08 (s, 2, —N=C—$\underline{CH_2}$); 4.10 (q, 2, —$OCH_2$—); 1.13 (t, 3, —$CH_3$).

*Trademark of Millipore Corporation and manufactured by Millipore Corporation, Waters Chromatography Division, 34 Maple Street, Milford, Mass. 01757, U.S.A.

EXAMPLES 8-12

Employing the procedure described in Example 7 with the appropriate alcohol yields the corresponding esters shown in Examples 8-12 below.

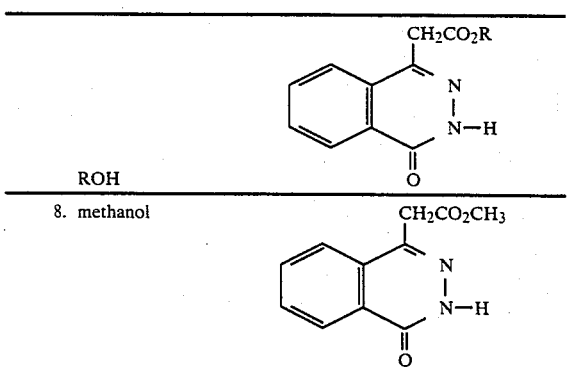

8. methanol

-continued

| | |
|---|---|
| ROH | 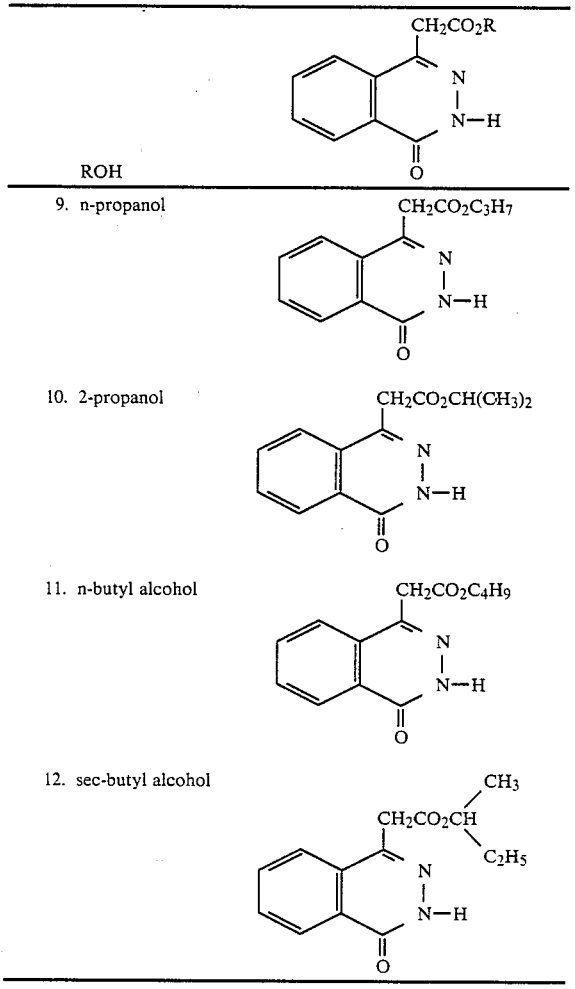 |
| 9. n-propanol | |
| 10. 2-propanol | |
| 11. n-butyl alcohol | |
| 12. sec-butyl alcohol | |

What is claimed is:

1. A process for the preparation of a compound of the formula

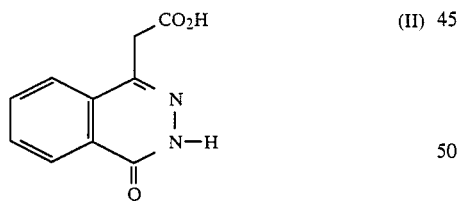 (II)

which comprises reacting a compound of the formula

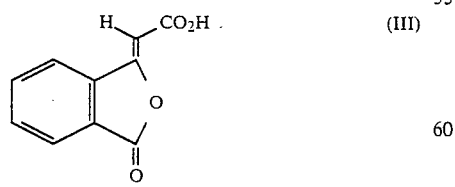 (III)

with hydrazine in the presence of a solvent; removing the unreacted hydrazine; and reacting the products so formed with acid in the presence of a solvent.

2. A process for the preparation of a compound of the formula

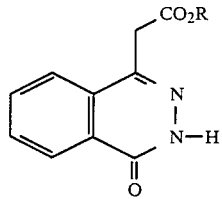 (IV)

wherein R is ($C_1$–$C_4$)alkyl which comprises the process according to claim 1 wherein the solvent is ROH and R is as defined above and adding additional acid.

3. The process according to claim 2 wherein about two mole equivalents of hydrazine are used and the acid is anhydrous hydrochloric acid.

4. The process according to claim 3 wherein the initial amount of anhydrous hydrochloric acid used is about 0.1 mole equivalent and the reaction with acid is heated to reflux temperature of the solvent.

5. The process according to claim 4 wherein R is $CH_3$ or $CH_2CH_3$.

6. The process according to claim 4 wherein the amount of additional anhydrous hydrochloric acid is about 1.0 mole equivalent.

7. A process for the preparation of a compound of the formula

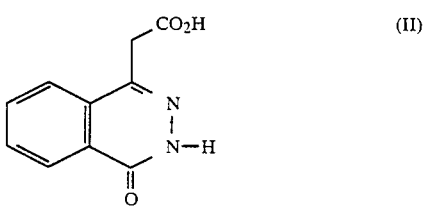 (II)

which comprises dissolving a compound of the formula

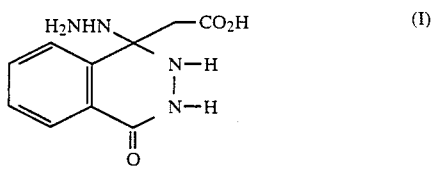 (I)

in water or aqueous NaOH and reacting with acid.

8. The process according to claim 7 wherein the acid is hydrochloric acid.

9. A process for the preparation of a compound of the formula

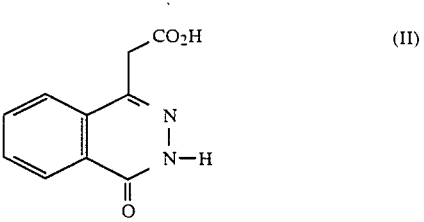 (II)

which comprises reacting a compound of the formula

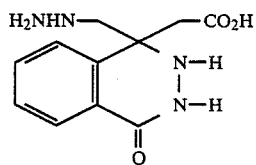

with acid in the presence of a solvent.

10. The process according to claim 9 wherein the acid is anhydrous hydrochloric acid.

11. The process according to claim 10 wherein the amount of anhydrous hydrochloric acid used is about 0.1 mole equivalent and the reaction is heated to reflux temperature of the solvent.

12. The process according to claim 11 wherein the solvent is methanol or ethanol.

13. The process according to claim 5 wherein the amount of additional anhydrous hydrochloric acid is about 1.0 mole equivalent.

14. The process according to claim 12 wherein about two mole equivalents of hydrazine are used and the acid is anhydrous hydrochloric acid.

15. The process according to claim 14 wherein the amount of anhydrous hydrochloric acid used is about 0.1 mole equivalent and the reaction is heated to reflux temperature of the solvent.

16. The process according to claim 15 wherein the solvent is methanol or ethanol.

17. The process according to claim 16 wherein the temperature of the reaction with hydrazine is controlled at less than about 40° C.

18. The process according to claim 16 wherein the temperature of the reaction with hydrazine is controlled to from about 25° C. to about 30° C.

19. The process according to claim 6 wherein the temperature of the reaction with hydrazine is controlled at less than about 40° C.

20. The process according to claim 6 wherein the temperature of the reaction with hydrazine is controlled to from about 25° C. to about 30° C.

21. The process according to claim 13 wherein the temperature of the reaction with hydrazine is controlled at less than about 40° C.

22. The process according to claim 13 wherein the temperature of the reaction with hydrazine is controlled to from about 25° C. to about 30° C.

* * * * *

UNITED STATES PATENT AND TRADEMARK OFFICE
CERTIFICATE OF CORRECTION

PATENT NO. : 4,904,782
DATED : February 27, 1990
INVENTOR(S) : Terry G. Sinay, Jr., et al.

It is certified that error appears in the above-identified patent and that said Letters Patent is hereby corrected as shown below:

Column 13, lines 1-9

"  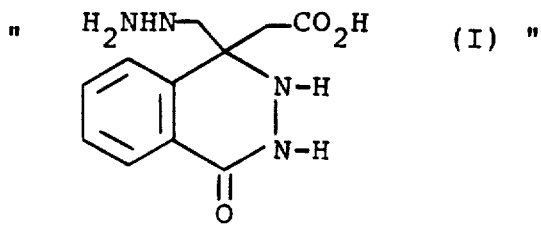   (I) "

should read

-- 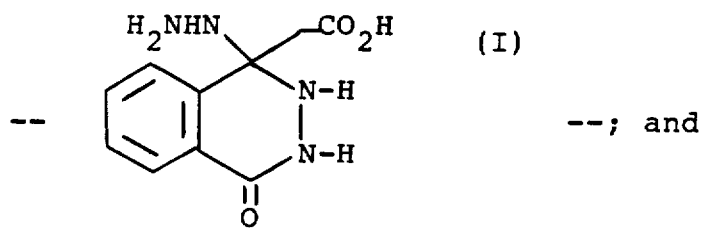   (I)   --; and

Column 13, line 23, "12" should read -- 1 --.

Signed and Sealed this

Sixteenth Day of April, 1991

*Attest:*

HARRY F. MANBECK, JR.

*Attesting Officer*  *Commissioner of Patents and Trademarks*